United States Patent [19]
Beavers

[11] Patent Number: 5,856,531
[45] Date of Patent: *Jan. 5, 1999

[54] PREPARATION OF 3-METHYTETRA-HYDROFURAN FROM 2,3-DIHYDROFURAN

[75] Inventor: William Anthony Beavers, Longview, Tex.

[73] Assignee: Eastman Chemical Company, Kingsport, Tenn.

[ * ] Notice: This patent issued on a continued prosecution application filed under 37 CFR 1.53(d), and is subject to the twenty year patent term provisions of 35 U.S.C. 154(a)(2).

[21] Appl. No.: 943,958

[22] Filed: Oct. 6, 1997

Related U.S. Application Data

[60] Provisional application No. 60/028,979 Oct. 21, 1996.

[51] Int. Cl.$^6$ ............. C07D 307/08; C07D 307/12
[52] U.S. Cl. ............. 549/497; 549/429; 549/508; 549/509
[58] Field of Search ................. 549/429, 497, 549/508, 509

[56] References Cited

U.S. PATENT DOCUMENTS

| | | | |
|---|---|---|---|
| 3,859,369 | 1/1975 | Copelin | 260/635 |
| 3,932,468 | 1/1976 | Kurkov | 260/346.1 |
| 4,590,312 | 5/1986 | Ernst | 568/861 |
| 4,879,420 | 11/1989 | Ernst | 568/617 |
| 5,536,854 | 7/1996 | Weyer et al. | 549/508 |

FOREIGN PATENT DOCUMENTS

| | | |
|---|---|---|
| 0 75 952 | 4/1983 | European Pat. Off. . |
| 0 727 422 | 8/1996 | European Pat. Off. . |
| 0 747 373 | 12/1996 | European Pat. Off. . |
| 3224033 | 1/1983 | Germany . |
| 79-135714 | 10/1979 | Japan . |
| 61-40227 | 2/1986 | Japan . |
| 8-133997 | 5/1996 | Japan . |
| 8-217708 | 8/1996 | Japan . |
| 8-217770 | 8/1996 | Japan . |
| 8-217771 | 8/1996 | Japan . |
| 8-291158 | 11/1996 | Japan . |
| 77-68106 | 6/1997 | Japan . |

OTHER PUBLICATIONS

Heterocycles, vol. 116, 1992; Abstract 12853p: V. Schiavo et al., Bull. Soc. Chim. Fr., 704 (1991).
F. Notheisz et al., J. Catal, 71, 331 (1981).
U. Gennari et al., Appl. Catal., 11, 341 (1984).
S. Teratini, Chem. Lett., 807 (1980).
R. Connor et al., J. Amer. Chem. Soc., 54, 4678 (1932).
H. Pines et al., J. Amer. Chem. Soc., 77, 5099 (1995).
A. R. Pinder, Synthesis, 425 (1980).

*Primary Examiner*—Ba K. Trinh
*Attorney, Agent, or Firm*—Michael J. Blake; Harry J. Gwinnell

[57] ABSTRACT

Disclosed is a two-step process wherein (1) 2,3-dihydrofuran is reacted with a trialkyl orthoformate in the presence of an acidic catalyst to produce a 2-alkoxy-3-(dialkoxymethyl)tetrahydrofuran intermediate and (2) the intermediate is contacted with hydrogen in the presence of a catalyst system comprising a Group VIII noble metal or rhenium and a strong acid to convert the intermediate to a mixture of 3-methyltetrahydrofuran (3-MeTHF) and 3-(hydroxymethyl)tetrahydrofuran (3-HOMeTHF). The 3-MeTHF produced in accordance with the present invention is useful as an industrial solvent and as a co-monomer in the manufacture of polymers such as elastomers. 3-HOMeTHF may be used as a solvent and in the manufacture of pharmaceutical and agricultural chemicals and acrylate and methacrylate esters for use in preparing polymers such as polyacrylates.

9 Claims, No Drawings

PREPARATION OF 3-METHYTETRAHYDROFURAN FROM 2,3-DIHYDROFURAN

This application claims the benefit of U.S. Provisional Application No. 60/028,979, filed Oct. 21, 1996.

This invention pertains to a process for the preparation of 3-methyltetrahydrofuran (3-MeTHF) and 3-(hydroxymethyl)tetrahydrofuran (3-HOMeTHF) from 2,3-dihydrofuran (2,3-DHF). More specifically, this invention pertains to a two-step process wherein (1) 2,3-DHF is reacted with a trialkyl orthoformate in the presence of an acidic catalyst to produce a 2-alkoxy-3-(dialkoxymethyl) tetrahydrofuran intermediate and (2) the intermediate is contacted with hydrogen in the presence of a catalyst system comprising a Group VIII noble metal, including compounds containing a Group VIII noble metal, and a strong acid to convert the intermediate to a mixture of 3-MeTHF and 3-HOMeTHF. The 3-MeTHF produced in accordance with the present invention is useful as an industrial solvent and as a co-monomer in the manufacture of polymers such as elastomers. 3-HOMeTHF also may be used as a solvent and in the manufacture of pharmaceutical and agricultural chemicals and acrylate and methacrylate esters for use in preparing polymers such as polyacrylates.

3-MeTHF has been produced in commercial quantities by the high pressure hydrogenation of citraconic anhydride and some of its derivatives according to the procedures most recently disclosed in U.S. Pat. No. 5,536,854 and Published Japanese Patent Application (Kokai) 08-217,771. Since citraconic acid is formed from citric acid or, more economically, as a minor by-product, during maleic anhydride production, these routes to 3-MeTHF are expensive and use a starting material which is not plentiful.

Processes for the production of 3-MeTHF based on less expensive precursors and precursors independent of the production of other materials have been developed. U.S. Pat. No. 3,859,369 discloses the preparation of 3-MeTHF by the hydroformylation of 2-buten-1,4-diol into 2-methyl-1,4-butanediol which is converted to 3-MeTHF by acid catalysis. U.S. Pat. Nos. 4,590,312 and 4,879,420 describe the conversion of 4-hydroxybutyraldehyde and its immediate precursor, 2-buten-1,4-diol, into 3-MeTHF by reductive alkylation with formaldehyde followed by acid catalyzed cyclization. In each case, the products are mixtures of 3-MeTHF and tetrahydrofuran. Mixtures are produced in the hydroformylation process because isomerization accompanies the hydroformylation, limiting the yield of 3-MeTHF by forming a tetrahydrofuran precursor. In the reductive alkylation processes, the intermediate products as well as the starting materials can form alcohols by hydrogenation. Only those hydrogenations occurring after an initial aldol condensation of the reactants with formaldehyde can form 3-MeTHF. All other hydrogenations gave tetrahydrofuran or other by-products.

Another method for the preparation of 3-MeTHF is disclosed in Published European Patent Application EP 727 422 and involves the hydrocyanation of methacrylate esters. A series of hydrolyses and esterifications forms a diester which may be reductively cyclized to 3-MeTHF using an acidic, copper chromite catalyst. In this case, not only are the starting materials expensive (although not as expensive as the citraconic anhydride derivatives), but the synthesis requires four steps. Japanese Published Patent Application (Kokai) JP 08-217,708 describes a process for producing 3-MeTHF by the hydroformylation of methacrylate esters to form mixtures of α- and β-formylisobutyrate esters using synthesis gas. Japanese Published Patent Application (Kokai) JP 08-217,770 discloses a similar hydroformylation using methyl formate as the C-1 source. In both of these hydroformylation processes, hydrogenation of the resulting β-formylisobutyrate ester over a copper chromite catalyst gives 3-MeTHF. One further hydroformylation route reported in Published European Patent Application Publication EP 747,373 consists of (1) the hydroformylation of isobutenyl alcohol (2-methyl-2-propen-1-ol) to form 4-hydroxy-3-methylbutyraldehyde which (2) is readily hydrogenated with nickel catalysts to 2-methyl-1,4-butanediol and which (3) is cyclized to 3-MeTHF by acid catalysis.

U.S. Pat. No. 3,932,468, describes a process for isomerizing isoprene monoepoxide into 4-methyl-2,3-dihydrofuran using a nickel and hydrohalic acid catalyst. Although the hydrogenation of 4-methyl-2,3-dihydrofuran into 3-MeTHF is relatively simple, the synthesis of the starting material, isoprene monoepoxide, is not. For example, the preparation of isoprene monoepoxide would require the use of classical (and expensive) epoxide manufacturing techniques such as the use of halohydrins or co-oxidation with aldehydes. Japanese Published Patent Application (Kokai) 08-291,158 describes another method for preparing 3-MeTHF in which propylene is converted into 2-methylsuccinate esters by a double oxidative carbonylation in the presence of an alcohol. Although the reductive cyclization of the 2-methylsuccinate esters to 3-methyltetrahydrofuran is facile, the double oxidative carbonylation reaction usually gives limited yields of the dicarbonylated products and requires expensive, reactive solvents to keep the reagents anhydrous.

Japanese Patent Publication (Kokai) JP 08-133,997 discloses the reaction of 2,3-dihydrofuran with orthoformate esters to make cyclopropane-1,1-dimethanol. In the first step of the process disclosed in Kokai JP 08-133,997 2,3-DHF is condensed with orthoformates in the presence of iron (III) chloride catalyst to obtain a 2-alkoxy-3-(dialkoxymethyl) tetrahydrofuran intermediate in a yield of 77%.

In the prior art pertaining to the hydrogenolysis of furan derivatives, V. Schiavo, et al., *Bull. Soc. Chim. Fr.*, 704 (1991), report the hydrogenation and hydrogenolysis of furan derivatives to tetrahydrofurans, acyclic ketones, and acyclic alcohols over copper, nickel, and several Group VIII metal-based catalysts. The hydrogenolysis reactions are promoted by acidic promoters, high temperatures and high hydrogen pressures. Platinum and ruthenium are particularly good hydrogenolysis catalysts and hydrogenolysis apparently is easier with furans than with tetrahydrofuran derivatives. F. Notheisz, et al., *J. Catal*, 71, 331 (1981) describe the hydrogenolysis of oxacycloalkanes over platinum, palladium, and nickel catalysts. They report that hydrogenolysis of the tetrahydrofurans occurred at the most accessible carbon, oxygen bond with all three metals capable of catalyzing hydrogenolysis at 60° to 300° C. U. Gennari, et al., *Appl. Catal.*, 11, 341 (1984), report further the decarbonylation of the initially-produced, tetrahydrofuran hydrogenolysis intermediates as well as the complete deoxygenation to hydrocarbons, even at temperatures as low as 100° C.

In contrast to the hydrogenolysis of furans and tetrahydrofurans, other ethers and alcohols undergo hydrogenolysis with varying degrees of difficulty. For example, Published Japanese Patent Application (Kokai) JP 79-135,714 discloses the Lewis acid-promoted hydrogenolysis of gem dialkoxy hydrocarbons catalyzed by supported rhodium and palladium catalysts under mild conditions producing ether products. Cleavage of the monoethers is much more difficult as shown by German Offenlegungsschrift DE 3,224, 033 which discloses the hydrogenolysis of both geminal and vicinal ethers using palladium catalysts. The product consists almost exclusively of materials from the cleavage at the geminal position with only small contributions from materials coming from cleavage at all other ether positions. Nevertheless, such ether cleavages are possible at harsher conditions [European Published Patent Application Publication EP 75,952] using a supported ruthenium catalyst to achieve hydrogenolysis at each ether and hydroxyl position to produce an array of products from diethylene glycol. Comparing catalyst efficiencies in this hydrogenolysis, S. Teratini, *Chem. Lett.*, 807 (1980), showed that palladium preferred to cleave C—O bonds (alcohols and ethers) compared with platinum which preferred to cleave C=O bonds.

The cleavage of alcohols is easier, although by no means facile. Thus, Japanese Published Patent Application (Kokai) JP 61 40,227 describes the use of palladium and alumina catalysts in the hydrogenolysis of alcohols containing aromatic rings to produce the corresponding hydrocarbons while keeping the aromatic rings intact. Japanese Published Patent Application (Kokai) JP 77-68,106 discloses the hydrogenolysis of alcohols into the corresponding hydrocarbons using palladium on activated carbon promoted with phosphotungstic acid. R. Conner, et al., *J. Amer. Chem. Soc.*, 54, 4678 (1932) describes the relative ease of hydrogenolysis of one of the alcohol groups in 1,3-diols compared with 1,2-, 1,4-, or other diols. However, H. Pines, et al., *J. Amer. Chem. Soc.*, 77, 5099 (1955) report that nickel supported kieselguhr catalyzes the hydrogenolysis of primary alcohols to the corresponding hydrocarbons containing one less carbon atom unless the catalyst is selectively poisoned with sulfur compounds.

Another method to accomplish the hydrogenolyses of both ethers and alcohols is to convert them into their corresponding alkyl halides under the reaction conditions. The conversion of the alkyl halides into the corresponding hydrocarbon is not difficult as is disclosed by A. R. Pinder, Synthesis, 425 (1980), using platinum and palladium catalysts. One possible, significant disadvantage to this route may be the adverse (poisoning) effect the halides may have on the hydrogenation catalysts, requiring the use of additional catalyst.

A process now has been developed for the preparation of 3-MeTHF and 3-HOMeTHF) from 2,3-DHF by two-step process wherein 2,3-DHF is reacted with a trialkylorthoformate ester in the presence of an acidic catalyst to produce a 2-alkoxy-3-(dialkoxymethyl)tetrahydrofuran intermediate and the intermediate is contacted with hydrogen in the presence of a catalyst system comprising a Group VIII noble metal (including compounds containing a Group VIII noble metal) or rhenium, water and a strong acid promoter to convert the intermediate to a mixture of 3-MeTHF and 3-HOMeTHF. The process may be modified to include an additional step using the same catalyst system under different conditions to convert 3-HOMeTHF into 3-MeTHF and thereby adjust the 3-MeTHF:3-HOMeTHF ratio. One embodiment of the present invention is a process for the preparation of a mixture of 3-MeTHF and 3-HOMeTHF which comprises the steps of:

(1) contacting 2,3-DHF with a trialkyl orthoformate having the formula

in the presence of an acidic catalyst to produce an intermediate compound having the formula

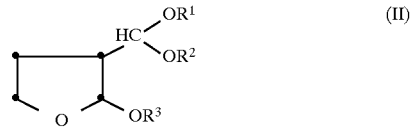

and (2) contacting the intermediate compound from step (1) with hydrogen and water in the presence of a catalytic amount of a Group VIII noble metal or rhenium and a strong acid;

wherein $R^1$, $R^2$ and $R^3$ are alkyl radicals, preferably unsubstituted alkyl of up to about 4 carbon atoms.

The acidic material useful for catalyzing the first step of the process may be selected from various Bronsted or Lewis acids. Examples of such Lewis acids include aluminum chloride, aluminum bromide, aluminum fluoride, aluminum iodide, boron trifluoride, boron trichloride, boron tribromide, boron triiodide, iron (III) fluoride, iron (III) chloride, iron (III) bromide, iron (III) iodide, tin (IV) fluoride, tin (IV) chloride, tin (IV) bromide, tin (IV) iodide, zinc fluoride, zinc chloride, zinc bromide, zinc iodide, titanium (IV) fluoride, titanium (IV) chloride, titanium (IV) bromide, titanium (IV) iodide, zirconium fluoride, zirconium chloride, zirconium bromide, and zirconium iodide. Examples of the include Bronsted acids as sulfuric acid, nitric acid, hydrogen fluoride, hydrogen chloride, hydrogen bromide, hydrogen iodide, phosphoric acid, trifluoroacetic acid, or toluenesulfonic acid. Because of its high activity and solubility, the most preferred catalyst is boron trifluoride introduced as its diethyl etherate complex.

The concentration of the acidic catalyst used in the process can be varied significantly depending, for example, on the particular catalyst used although only low concentrations usually are needed. By adjusting the reaction conditions, any concentration from 0.1 ppm to 50 weight percent for liquid or saturation for solid catalysts, based on the weight of the step (1) reaction mixture, may be used.

Under the conditions of step (1), acetals, i.e., 1,1-dialkoxy-substituted compounds, also can add to 2,3-DHF just as orthoformate esters, i.e., 1,1,1-trialkyl-substituted compounds, can. Because intermediate (II) itself is an acetal, it is capable of adding additional 2,3-DHF to form higher adducts of orthoformate (I) to 2,3-DHF. In fact, intermediate (II) can be considered the first stage of a living polymerization in which orthoformate (I) and 2,3-DHF combine to form 1:1 adducts, 1:2 adducts, 1:3 adducts, 1:4 adducts, and higher ratio adducts with the ratios shifting to adducts higher that 1:1 as 2,3-DHF continues to be added. To optimize formation of intermediate (II) relative to the higher adducts requires catalyst concentrations sufficiently high to make 2,3-DHF, rather than the catalyst, the rate limiting reagent. In this case, the 2,3-DHF reacts immediately with any of an array of pendant carbonium ions from orthoformate/catalyst complexes to form an intermediate (II)/catalyst complex. Although this complex can continue reacting to form even higher adducts, formation of higher adducts is inhibited by the presence of a large amount of compound (I)/catalyst complex competing for the limited supply of 2,3-DHF. Consequently, very little 2,3-DHF becomes incorporated into higher adducts. Maintaining low 2,3-DHF concentrations throughout the reaction results in the formation of the 1:1 adduct, intermediate (II). In comparison with too low a catalyst concentration, the initially-formed and limited orthoformate/catalyst complex reacts with an abundance of 2,3-DHF to form an intermediate (II)/catalyst complex. With very little competing orthoformate (I)/catalyst complex, the intermediate (II)/catalyst complex can continue adding 2,3-DHF, possibly adding several units before the reaction stops. The only thing stopping the addition is the transfer of the catalyst component of the complex to an unoccupied orthoformate (I) to restart the cycle. This result has allowed the 2,3-DHF concentration to rise to moderate levels throughout the reaction and has allowed the formation of many products, intermediate (II) and several of the higher adducts. These factors dictate a lower end of the preferred catalyst concentration range of about 200 ppm, 0.02 weight percent.

Other factors determine the upper end of the preferred catalyst range. The use of excessively high concentrations of catalyst causes an increase in the activity of the carbonium ions from orthoformate (I) forming an alcohol, $HOR^1$, and a carbene, $R^2O-C-OR^3$. Carbenes can insert into random C—H bonds and react with other carbenes to form tetraalkoxy ethylene, $(R^2O)_2C=C(OR^3)_2$, which in turn can oligomerize to form new sets of by-products. In addition, the high activity carbonium ions in the medium eventually react with intermediate (II) and other products to form alcohols and vinyl ethers. Since 2,3-DHF is a vinyl ether, these compounds will react similarly with orthoformate (I) to form adducts containing higher amounts of orthoformate (I). This effect has two consequences: First, catalyst must be removed or neutralized from the reaction mixture within a few hours of the completion of the addition to keep these new byproducts out. Second, the practical upper limit on the preferred concentration is about 4000 ppm, 0.4 weight percent. Furthermore, the time during which the catalyst and intermediate (II) are permitted to be in contact should be limited, e.g., to 6 hours or less, to minimize formation of by-products.

To further minimize by-product formation, the mole ratio of total orthoformate (I) to 2,3-DHF normally should be in the range of 1:1 to 100:1. Because of material handling costs and the energy required to separate and recycle the unreacted orthoformate (I), the most preferred orthoformate (I):2,3-DHF mole ratio is 2:1 to 10:1. The first step of the reaction is carried out under substantially anhydrous conditions imposed by the sensitivity of orthoformate esters to decomposition by water. The alkyl groups represented by $R^1$, $R^2$, and $R^3$ preferably contain up to about 6 carbon atoms. $R^1$, $R^2$, and $R^3$ most preferably are each methyl.

The optimum temperature at which step (1) may be carried out can vary significantly, depending on such factors as catalyst and reagent concentrations. Step (1) reaction temperatures can range from about −20° to 100° C. although the higher temperatures favor increased by-product formation and shortened contact times of catalyst with products. Thus, the use of temperatures in the range of about −10° to 20° C. normally are most preferred.

In the second step of the process, the intermediate compound of formula (III) is subjected to a combined hydrolysis/hydrogenation/hydrogenolysis and converted to a mixture of 3-MeTHF and 3-HOMeTHF by the removal of all the alkoxy groups while not affecting the tetrahydrofuran ring. The hydrolysis/hydrogenation/hydrogenolysis is carried out by contacting intermediate compound (III) with hydrogen and water in the presence of a catalytic amount of a Group VIII noble metal and a strong acid under hydrolysis/hydrogenation/hydrogenolysis conditions of temperature and hydrogen pressure.

Palladium, platinum, ruthenium, rhenium, rhodium and iridium are examples of catalytic metals which may be used in the second step of the present process. The form of the Group VIII noble metal or rhenium catalyst is not critical although the most efficient use of the expensive Group VIII noble or rhenium metal is in a finely divided form on an appropriate support. Normally, supported Group VIII noble metal or rhenium catalysts comprise about 0.1 to 10 weight percent metal deposited on a suitable catalyst support material such as activated charcoal, silica, alumina, titania, zirconia, barium sulfate, and calcium sulfate. Alternatively, a Group VIII noble metal in a finely divided form, e.g., palladium black, may be used even though it might not represent the most efficient use of the expensive noble metal. Also, salts such the chlorides, fluorides, bromides, nitrates, and carboxylates, e.g., acetate or benzoate; oxides; or hydroxides of Group VIII noble metals may be used. In addition to these soluble salts, insoluble salts such as phosphates, sulfates, or iodides can be used. Supported catalysts comprising about 1 to 20 weight percent palladium on carbon, e.g., activated charcoal or graphite, or silica are the most preferred catalysts.

The amount of the Group VIII noble metal or rhenium catalyst which is catalytically effective may vary significantly depending upon the particular metal used, the form in which it is used, the mode in which the process is operated and other process variables such as temperature, pressure and residence time. For example, the amount of palladium present may be from 0.000001 to more than 100 mole percent based on the moles of intermediate compound (II) present. The amount of palladium present preferably is about 0.001 to 20, most preferably 0.1 to 10, mole percent based on the moles of intermediate compound (II) present.

Examples of the strong acids which may be used in the second step of the process include sulfuric, phosphoric, nitric, hydrofluoric, hydrochloric, hydrobromic, hydriodic, trifluoroacetic, or a sulfonic acid such as alkylsulfonic acids, arylsulfonic acids, e.g., toluenesulfonic acids, and polymeric sulfonic acids, e.g., acidic ion exchange resins comprising styrene/divinylbenzene polymers bearing sulfo groups. The concentration of the monomeric strong acids may be in the range of 0.000001 molar to 16 molar although concentrations of 0.01 molar to 1 are preferred and concentrations of 0.05 to 0.5 molar are most preferred. When using the preferred amounts of palladium and strong acid, the mole ratio of palladium to strong acid is in the range of about 1:10 to 1:100. The second step of the present process preferably is operated in the presence of a strong acid in a concentration which gives the reaction mixture a pH of less than about 4, most preferably a pH in the range of about 0 to 2.

The amount of water used in the second step may be in the range of 2 to 1000 moles water per mole of intermediate (II). The amount of water used preferably is in the range of about 10 to 100 moles water per mole of intermediate (II). Step (2) may be carried out at a temperature of about 0° to 350° C. and a hydrogen pressure of about 1 to 1000 bars absolute (about 0 to 14,5000 psig). The preferred operating temperature range is about 50° to 250° C. and most preferably about 70° to 180° C. The preferred hydrogen pressure range is about 4 to 70 bars absolute (about 43 to 1000 psig) and most preferably about 8 to 50 bars absolute (about 100 to 710 psig). The product of the second step comprises a mixture of 3-MeTHF and 3-HOMeTHF usually in a 3-MeTHF:3-HOMeTHF mole ratio of about 0.2:1 to 5:1.

The use of one or more inert solvents is permissible, although not essential, in both steps of the present invention.

The use of different catalysts and conditions will influence the selectivities and mole ratios of 3-MeTHF to 3-HOMeTHF so that either can become the predominant or exclusive product. Thus, for preparing 3-HOMeTHF exclusively, relative mild hydrogenation/hydrogenolysis conditions should be used whereas the preparation of 3-MeTHF exclusively requires the use of a harsher combination of conditions, producing only hydrogenolysis. However, the use of such harsher conditions may result in the hydrogenolysis of the tetrahydrofuran ring. Therefore, to improve the overall yield of 3-MeTHF, the reaction mixture obtained from step (2) may be subjected to a rapid steam distillation to remove 3-MeTHF, a 3-(alkoxymethyl) tetrahydrofuran having the formula

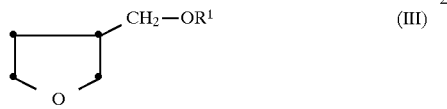

(III)

and 3-formyltetrahydrofuran [compound (IV)] giving a undistilled residue containing almost all of the 3-HOMeTHF. This distillation residue, recovered compounds (III) and (IV), and any unreacted and recycled 3-HOMeTHF from the step (3) hydrogenolysis are combined under the harsher hydrogenolysis conditions to give 3-MeTHF in overall yield improved over a one step hydrogenolysis. These harsher conditions are represented by temperatures about 100° to 150° C. above those employed in step (2). Thus, the hydrogenolysis carried out subsequent to step (2) using harsher hydrogenolysis conditions is carried out at a temperature of about 150° to 350° C., preferably about 200° to 300° C.

The process of the present invention is further illustrated by the following examples. As used herein, the percent conversion of a reactant is:

$$\frac{\text{Moles Reactant Converted}}{\text{Moles Reactant Fed}} \times 100$$

and the percent selectivity to a particular compound:

$$\frac{\text{Moles Reactant Converted to the Compound}}{\text{Moles Reactant Converted}} \times 100$$

EXAMPLE 1

The apparatus used in the first step of the process consisted of a flame-dried, 500 mL, round-bottom flask equipped with a flame-dried addition funnel, a thermowell with thermometer, a side arm covered with a septum cap, an overhead stirrer, and a reflux condenser topped with a gas inlet fitting through which a dry nitrogen blanket was introduced and maintained throughout the reaction. To this flask was charged by cannula through the septum cap 240 mL of anhydrous trimethyl orthoformate (d=0.970, 233 g, 2.19 moles). After starting rapid stirring and cooling 5° C., a catalyst charge of 0.2 mL of boron trifluoride diethyl etherate (d=1.154, 0.23 g, 1.6 millimole—mmol) was added through the septum cap. This quantity of catalyst gave a $BF_3$ concentration of 460 ppm. The addition funnel was charged with 75 mL of anhydrous 2,3-DHF (freshly distilled from calcium hydride; d=0.927, 69 g, 0.99 mole) and 85 mL of anhydrous trimethyl orthoformate (0.78 mole). The molar ratio of the total trimethyl orthoformate to the 2,3-DHF was 2.99. The contents of the addition funnel were added to the reaction flask over a period of 150 minutes with rapid stirring while maintaining the temperature at 5° C. to 15° C. Stirring was continued for 5 minutes after completion of the addition. Gas chromatographic (GC) analysis of the reaction mixture showed a 99.6% conversion of the 2,3-DHF a selectivity to 2-methoxy-3-(dimethoxymethyl) tetrahydrofuran of 93.1% and a selectivity to bis(2-methoxytetrahydrofuran-3-yl)methoxymethane (the 2:1 adduct) of 5.8%. There was also detected several isomers of the 3:1 adduct present in a selectivity of 0.8%.

The desired product, 2-methoxy-3-(dimethoxymethyl) tetrahydrofuran, was isolated by vacuum distillation at 83.5°–85.5° C./12 mm Hg or 74.0°–75.5° C./7 mm Hg. The 2:1 adduct by-product, bis(2-methoxy-tetrahydrofuran-3-yl) methoxymethane), was isolated by vacuum distillation at 128°–134°C./6 mm Hg.

EXAMPLE 2

The procedure described in Example 1 was repeated except that (1) the reaction temperature range was −10° to −7° C., (2) the initial catalyst concentration was 345 ppm representing 1.2 mmol $BF_3$ present, and (3) the addition time was 90 minutes. The selectivity to the 1:1 adduct, 2-methoxy-3-(dimethoxymethyl)tetrahydrofuran, was 81.7% and the selectivity to the 2:1 adduct was 14.8%. After stirring an additional 12 hours at room temperature with the catalyst still present, the reaction mixture had darkened from water-white to dark amber with the selectivity to the 1:1 adduct having fallen to 78.4% and the selectivity to the 2:1 adduct having fallen to 13.9%.

Based on this product deterioration, in all experiments subsequent to Example 2 the catalyst was neutralized within one hour after adding the last of the reagents by adding three molar equivalents of anhydrous sodium hydroxide solution to the reaction mixture. In this Example 2, the neutralization required 0.67 g of 22 weight percent methanolic sodium hydroxide representing 3.7 mmol added to neutralize the 1.2 mmol of $BF_3$ present. GC analysis of the reaction mixture at this point showed no change over several days. The workup consisted of fractionally distilling this mixture at atmospheric pressure until the base temperature reached 120° C., cooling the pot residue to ambient temperatures, vacuum filtering the salts away from the cooled pot residue, and fractionally distilling the filtrate under reduced pressures. The distillate collected at atmospheric pressure consisted of 97.8 area percent trimethyl orthoformate which, after the removal of 2.2 percent of low boilers by fractional distillation, was suitable for the preparation of additional 2-methoxy-3-(dimethoxymethyl)tetrahydrofuran.

This example shows a different set of conditions for conducting the step (1) reaction and to illustrate recovery and purification of the unreacted trimethyl orthoformate for recycle to other 2-methoxy-3-(dimethoxymethyl) tetrahydrofuran preparations.

EXAMPLE 3

The procedure of Example 1 was repeated using a temperature range of 65°–95° C., an initial catalyst concentration of 557 ppm $BF_3$ and a reagent addition time of 145 minutes. GC analysis of the resulting product showed a 78.0% selectivity to the 1:1 adduct of 2,3-DHF:trimethyl orthoformate and a 10.3% selectivity to the 2:1 adduct. GC/mass spectral analysis of this mixture showed the presence of several additional by-products including acyclic olefins, vinyl ethers, and 1:2, 1:3, 2:2, and 3:2 adducts of 2,3-DHF:trimethyl orthoformate not found in Examples 1 and 2.

EXAMPLE 4

The procedure of Example 1 was repeated except the scale was increased by a factor of 10, the reaction temperature range was −13° to −8° C., the initial catalyst concentration was 75 ppm of $BF_3$, and the mole ratio of total trimethyl orthoformate:2,3-DHF was 3.48. The reagent addition time was 160 minutes. GC analysis of the resulting product showed a 66.5% selectivity to the 1:1 2,3-DHF:trimethyl orthoformate adduct and a 23.1% selectivity to the 2:1. Also detected were the 3:1 adduct (7.7% selectivity) the 4:1 adduct (1.2% selectivity) and a trace of the 5:1 adduct.

EXAMPLE 5

The procedure described in Example 4 was repeated except the temperature range was −5° to 3° C., the initial catalyst concentration was 1501 ppm $BF_3$, 70% of the trimethyl orthoformate was recycled from a prior experiment and the reagent addition time was 185 minutes. GC analysis of the resulting product showed a 98.1% selectivity to the 1:1 adduct of 2,3-DHF and trimethyl orthoformate, a 0.7% selectivity to 2:1 adduct, and a 0.6% selectivity to the 3:1 adduct.

EXAMPLES 6–10

The procedures described in the preceding examples were repeated using different mole ratios of trimethyl orthoformate:2,3-DHF (Reactant Ratio), reaction temperature range (Temp Range—°C.), reagent addition times (Addn Time—hours) and $BF_3$ concentrations (Cat Conc). These variables and the selectivities to the 1:1, 2:1, 3:1 and 4:1 adducts are set forth in Table I. The amounts of materials and conditions used in Examples 1–5 and the results obtained in those examples also are shown in Table I.

TABLE I

| Example No. | Reactant Ratio | Temp | Addn Time | Cat Conc | Selectivity to Adducts | | | |
|---|---|---|---|---|---|---|---|---|
| | | | | | 1:1 | 2:1 | 3:1 | 4:1 |
| 1 | 2.99 | 5–15 | 2.5 | 400 | 92.8 | 5.9 | 1.3 | 0 |
| 2 | 3.09 | −10—7 | 1.5 | 345 | 81.7 | 14.8 | 3.3 | 0.1 |
| 3 | 2.98 | 45–95 | 2.4 | 557 | 78.0 | 10.3 | 2.3 | 0 |
| 4 | 3.48 | −13—7 | 2.7 | 75 | 66.5 | 23.1 | 7.7 | 1.2 |
| 5 | 3.49 | −5–3 | 3.1 | 1501 | 98.1 | 0.7 | 0.6 | 0 |
| 6 | 3.51 | −5–0 | 2.3 | 1126 | 97.5 | 1.0 | 0.3 | 0 |
| 7 | 3.01 | −15—10 | 2.4 | 599 | 92.3 | 7.1 | 0 | 0 |
| 8 | 3.02 | −7–9 | 2.2 | 506 | 93.6 | 6.2 | 0.2 | 0 |
| 9 | 2.68 | −8—2 | 2.6 | 1132 | 97.5 | 0.9 | 0.4 | 0 |
| 10 | 2.42 | −10—6 | 2.5 | 1840 | 98.5 | 0.5 | 0 | 0 |

EXAMPLE 11

To a 300 mL, stainless steel autoclave was charged 20 mL of 2-methoxy-2-(dimethoxymethyl)tetrahydrofuran (d=1.0524, 21 g, 0.119 mole), 100 mL distilled water, 1.0 mL of concentrated sulfuric acid (d=1.84, 1.8 grams, 18 mmol), and 5.0 g of 5 weight percent palladium on activated charcoal. The autoclave was sealed and the reaction began by stirring and heating the contents to 140° C. for 1 hour under a hydrogen pressure of 34 bars. At the end of this time, GC analysis of the contents of the autoclave showed a 99.1% conversion of the starting material. There were two primary products: 3-MeTHF present in a selectivity of 45.9% and 3-HOMeTHF in a selectivity of 47.6%. Also present was the theoretical 11.5 grams of methanol from the hydrolysis/hydrogenolysis of the intermediate acetal (II).

EXAMPLE 12

Example 11 was repeated substituting 1.01 g of iodine (4.0 mmol) for the sulfuric acid. All other conditions were the same. Analysis of the reaction mixture after two hours reaction showed the same two products as in Example 11 but in different selectivities: 37.6% selectivity to 3-MeTHF and 56.4% selectivity to 3-HOMeTHF.

This experiment shows the effect of using another strong acid on the product distribution. Under the reaction conditions, iodine reacts with hydrogen to form hydrogen iodide.

EXAMPLE 13

Example 11 was repeated except the catalyst was 5.14 g of 5 weight percent platinum on activated charcoal and the strong acid was 1 weight percent phosphoric acid. Analysis of the reaction mixture after one hour at 180° C. showed a 36.5% selectivity to 3-MeTHF and a 41.5% selectivity to 3-HOMeTHF.

EXAMPLE 14

Example 11 was repeated except the catalyst was 1.04 g of 5 weight percent rhodium on activated charcoal and the strong acid was 1 percent phosphoric acid. GC analysis of the reaction mixture after one hour at 150° C. showed a 40.2% selectivity to 4-methyl-2,3-dihydrofuran (4-MeDHF, an immediate precursor to 3-MeTHF), a 2.1% selectivity to 3-MeTHF, a 20.0% selectivity to 3-formyltetrahydrofuran (3-FTHF, Compound IV, an immediate precursor to 3-HOMeTHF), and a 19.7% selectivity to 3-HOMeTHF.

EXAMPLE 15

Example 11 was repeated except the catalyst was 0.99 gram of 5 weight percent iridium on activated charcoal and the strong acid was phosphoric acid. GC analysis of the reaction mixture after one hour at 170° C. showed the following selectivities: 0.8% to 4-MeDHF, 0.2% to 3-MeTHF, 11.4% to 3-FTHF, and 0.9% to 3-(methoxymethyl)tetrahydrofuran (3-MeOMeTHF, Compound III). The majority of the material balance for this catalyst was heavier byproducts and light hydrocarbons.

EXAMPLE 16

Example 11 was repeated except the 5.0 g of 5% palladium on activated charcoal was replaced by 2.5 g of 10 weight percent palladium on activated charcoal. GC analysis of the reaction mixture after 1 hour at 150° C. showed a 62.5% selectivity to 3-MeTHF and a 28.4% selectivity to 3-HOMeTHF. This experiment shows the effect of changing the catalyst loading while keeping the total palladium content constant on the product distribution.

EXAMPLE 17

Example 16 was repeated except that the hydrogenolysis was performed at 150° C. for 1 hour and then at 200° C. for 1 hour. GC analysis of the reaction product showed a 65.8% selectivity to 3-MeTHF and a 27.9% selectivity to 3-HOMeTHF.

EXAMPLE 18

To a nitrogen-flushed, 2-liter, Parr autoclave was charged 300 mL of 2-methoxy-3-(dimethoxymethyl)tetrahydrofuran (d=1.0524, 316 g, 1.792 moles), 10.01 g of 5 weight percent palladium on activated charcoal, 6.51 mL of 85 weight percent phosphoric acid (d=1.685, 9.32 g $H_3PO_4$, 95.1 mmol), and 1000 mL of deionized water. After sealing the autoclave, the contents were stirred vigorously at ambient temperatures for 1 hour under a hydrogen pressure of 34 bars which was maintained throughout the reaction. During this time, the pressure consumption amounted to 85 bars. At this time, the contents were heated with continued vigorous stirring to 100° C. and were maintained at this temperature for 2 hours. During this time, the hydrogen consumption amounted to an additional 89.5 bars. Finally, the contents were heated with continued vigorous stirring to 140° C. and were maintained at this temperature for 5 hours. During this time, the hydrogen consumption amounted to an additional 23.5 bars.

GC analysis of the final reaction mixture showed a 100% conversion of starting material. The selectivity to 3-MeTHF was 59.2% and the selectivity to 3-HOMeTHF was 29.8%. Also present was 3-MeOMeTHF (3.8% selectivity) 3-FTHF (2.3% selectivity), 4-MeDHF (0.1% selectivity) and 0.1 percent tetrahydrofuran (THF—0.1% selectivity). The total yield of useful products which are convertible into either 3-MeTHF or 3-HOMeTHF was 95.1 percent.

EXAMPLES 19–25

Example 18 was repeated using a catalyst system of 10.01 g of 5 weight percent palladium on activated charcoal and 6.51 mL of 85 weight percent phosphoric acid and a variety of temperatures (°C.) and times and amounts of starting materials. These variables are shown in Table II wherein the values given for TMOF and Water refer to the amounts (mL) of trimethyl orthoformate reactant and deionized water used in each example.

TABLE II

| Example No. | Periods of Heating | TMOF | Water |
|---|---|---|---|
| 19 | 3.0 hours at 110 & 4.3 hours at 150 | 300 | 1000 |
| 20 | 3.0 hours at 90 & 5.0 hours at 140 | 300 | 1000 |
| 21 | 3.0 hours at 100 & 5.0 hours at 140 | 300 | 1000 |
| 22 | 2.0 hours at 100 & 5.1 hours at 140 | 400 | 1000 |
| 23 | 2.0 hours at 100 & 5.0 hours at 140 | 250 | 1000 |
| 24 | 2.0 hours at 100 & 5.0 hours at 140 & 2.0 hours at 160 | 250 | 1000 |
| 25 | 2.0 hours at 100 & 0.7 hours at 140 | 225 | 1000 |

The compounds formed in Examples 19–25, and the selectivities in which they were formed, are shown in Table III wherein ΔPress is the total hydrogen pressure drop (hydrogen uptake—bars) and AA refers to various acyclic alcohols including 1-butanol, 3-buten-1-ol, 2-methyl-1-butanol, 3-methyl-1-butanol, 2-methyl-3-buten-1-ol, and 3-methyl-3-buten-1-ol.

TABLE III

| Example No. | Δ Press | AA | THF | 4-Me DHF | 3-Me THF | 3-MeOMe THF | 3-F THF | 3-HOMe THF |
|---|---|---|---|---|---|---|---|---|
| 19 | 139.4 | 0.1 | 0.8 | 0.2 | 58.4 | 6.5 | 3.4 | 24.3 |
| 20 | 121.9 | 0.4 | 0.3 | 0.2 | 51.0 | 5.7 | 8.9 | 30.8 |
| 21 | 128.8 | 0 | 0.3 | 0.1 | 49.8 | 7.9 | 4.4 | 35.5 |
| 22 | 204.8 | 0.1 | 1.6 | 0.5 | 47.5 | 5.3 | 17.0 | 10.6 |
| 23 | 101.7 | 0.2 | 0.2 | 0 | 55.9 | 4.9 | 1.6 | 33.2 |
| 24 | 100.7 | 0.4 | 0.2 | 1.8 | 61.0 | 5.5 | 2.7 | 15.8 |
| 25 | 78.8 | 0.1 | 0.2 | 0 | 56.7 | 3.4 | 7.0 | 27.7 |

EXAMPLE 26

The combined reaction products from Examples 18–25 were subjected to steam distillation to remove about one-half of the water with the organics. Analysis of the undistilled residue showed a total organic content of 18.6%. The phosphoric acid content was 1.9 weight percent (0.19M). The composition of the organic portion of the residue consisted primarily of 3.1% 3-FTHF and 86% 3-HOMeTHF. It also contained 0.6% methanol, 0.2% 3-MeTHF, 0.2% 3-MeOMeTHF, 7.6% heavy by-products and 2.3 and a variety of other light intermediate hydrogenolysis products which may be further hydrogenolyzed to 3-MeTHF and/or 3-HOMeTHF.

To a nitrogen-flushed, 300-mL, stainless steel autoclave was charged 100 mL of the undistilled residue described in the preceding paragraph (d=1.0209, 103 g, 16.3 g 3-HOMeTHF, 0.16 mole) and 1.02 g of 5 weight percent palladium on activated charcoal. After sealing the autoclave and charging 34 bars of hydrogen pressure, rapid stirring of the contents of the autoclave was begun and continued throughout the reaction. The contents were heated to 280° C. and maintained at that temperature for 1 hour at which time GC analysis of the autoclave contents showed a 28.8% conversion of the 3-HOMeTHF initially present with a 54.7 selectivity to 3-MeTHF. Also formed were THF (selectivity=1.4%), 4-MeDHF (selectivity=1.7%), light, acyclic alcohols (selectivity=1.2%), heavy by-products (selectivity=17.8%) and light hydrocarbons and ethers (selectivity=23.2%).

EXAMPLE 27

Example 26 was repeated except that 1.00 g of 5 weight percent iridium on activated charcoal was used as the catalyst. Analysis of the reaction mixture after 1 hour at 290° C. showed a 21.6% conversion of the starting material and a selectivity to 3-MeTHF of 19.5%. Also formed were THF (selectivity=1.0%), 4MeDHF (selectivity=0.9%), light acyclic alcohols (selectivity=0.7%), heavy by-products (selectivity=50.4%) and light hydrocarbons and ethers in (selectivity=27.5%).

EXAMPLE 28

Example 26 was repeated except the catalyst used was 1.00 g of 5 weight percent rhodium on activated charcoal. Analysis of the reaction mixture after 1 hour at 280° C. showed a 3-HOMeTHF conversion of 23.7 percent with a selectivity to 3-MeTHF of 36.7%. Also produced were THF (selectivity=1.7%), 4-MeDHF (selectivity=1.7%), light acyclic alcohols (selectivity=1.2%), heavy by-products (selectivity=31.8%) and light hydrocarbons and ethers (selectivity=26.95).

The invention has been described in detail with particular reference to preferred embodiments thereof, but it will be understood that variations and modifications may be effected within the spirit and scope of the invention.

I claim:

1. Process for the preparation of a mixture of 3-methyltetrahydrofuran (3-MeTHF) and 3-(hydroxymethyl)tetrahydrofuran (3-HOMeTHF) which comprises the steps of:

(1) contacting 2,3-dihydrofuran (2,3-DHF) with a trialkyl orthoformate having the formula

in the presence of an acidic catalyst to produce an intermediate compound having the formula

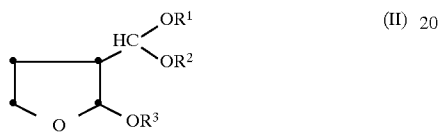

and (2) contacting the intermediate compound from step (1) with hydrogen and water in the presence of a catalytic amount of a Group VIII noble metal or rhenium and a strong acid;

wherein $R^1$, $R^2$ and $R^3$ are alkyl radicals.

2. Process according to claim 1 wherein step (1) is carried out at a temperature of about −20° to 100° C., the acidic catalyst is selected from Bronsted and Lewis acids and the mole ratio of total orthoformate (I) to 2,3-DHF is in the range of about 1:1 to 100:1 and step (2) is carried out at a temperature of about 50° to 250° C. and a hydrogen pressure of about 4 to 70 bars absolute in the presence of a catalytic metal selected from palladium, platinum, ruthenium, rhenium, rhodium and iridium.

3. Process according to claim 2 wherein step (2) is carried out in the presence of a strong acid at a pH of less than about 4.

4. Process according to claim 2 wherein $R^1$, $R^2$ and $R_3$ are independently selected from alkyl of up to about 4 carbon atoms.

5. Process for the preparation of a mixture of 3-methyltetrahydrofuran (3-MeTHF) and 3-(hydroxymethyl)tetrahydrofuran (3-HOMeTHF) which comprises the steps of:

(1) contacting 2,3-dihydrofuran (2,3-DHF) with a trialkyl orthoformate having the formula

in the presence of in the presence of an acidic catalyst selected from Bronsted and Lewis acids at a temperature of about −10° to 20° C. in an orthoformate (I):2,3-DHF mole ratio of 2:1 to 10:1 to produce an intermediate compound having the formula

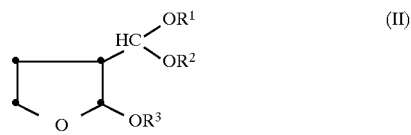

and (2) contacting the intermediate compound from step (1) with hydrogen and water in the presence of a catalytic amount of a Group VIII noble metal selected from palladium and platinum and a strong acid selected from sulfuric, phosphoric and sulfonic acids at a temperature of about 70° to 180° C. and a hydrogen pressure of about 8 to 50 bars absolute;

wherein $R^1$, $R^2$ and $R_3$ are independently selected from alkyl of up to about 4 carbon atoms.

6. Process according to claim 5 wherein step (2) is carried out in the presence of phosphoric acid at a pH of about 0 to 2.

7. Process according to claim 5 wherein step (1) is carried out in the presence of an acidic catalyst selected from aluminum trichloride, aluminum tribromide, aluminum trifluoride, aluminum triiodide, boron trifluoride, boron trichloride, boron tribromide, boron triiodide, iron (III) chloride, iron (III) bromide, iron (III) fluoride, iron (III) iodide, tin (IV) chloride, tin (IV) bromide, tin (IV) fluoride, tin (IV) iodide, titanium (IV) fluoride, titanium (IV) chloride, titanium (IV) bromide, titanium (IV) iodide, zirconium tetrachloride, zirconium tetrabromide, zirconium tetrafluoride, zirconium tetraiodide, sulfuric acid, hydrogen chloride, hydrogen bromide, hydrogen iodide, hydrogen fluoride, phosphoric acid, trifluoroacetic acid, and toluenesulfonic acid.

8. Process according to claim 7 wherein step (1) is carried out in the presence of boron trifluoride and $R^1$, $R^2$ and $R_3$ each is methyl.

9. Process according to claim 8 wherein step (2) is carried out in the presence of a supported palladium catalyst.

* * * * *